(12) United States Patent
Uchino et al.

(10) Patent No.: US 6,197,292 B1
(45) Date of Patent: *Mar. 6, 2001

(54) THERAPEUTIC AGENT AND TREATMENT FOR CANINE INTRACTABLE DERMATITIS

(75) Inventors: Tomiya Uchino, Tokyo; Katsushige Yamada, Aichi; Fumiyoshi Okano, Nagoya; Masahiro Satoh, Kamakura; Isao Kawakami, Tokyo, all of (JP)

(73) Assignee: Toray Industries, Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/240,004

(22) Filed: Jan. 29, 1999

Related U.S. Application Data

(63) Continuation-in-part of application No. 09/001,944, filed on Dec. 31, 1997, now Pat. No. 5,955,069.

(30) Foreign Application Priority Data

Mar. 6, 1997 (JP) .................................................... 9-51612

(51) Int. Cl.⁷ ............................. A61K 38/21; C12P 21/02
(52) U.S. Cl. ...................................... 424/85.5; 435/69.51
(58) Field of Search ......................... 424/85.5; 435/69.51

(56) References Cited

U.S. PATENT DOCUMENTS 5,955,069 * 9/1999 Uchino et al. ...................... 424/85.5

OTHER PUBLICATIONS

Wetzel, R., et al. (1990) *Protein Engr.* 3(7): 611–23; corrigendum, Id. 4(1):105.*
Nishioka et al., *J. Dermatol.*, vol. 22, pp. 181–185 (1995).
Williams, Br., *J. Dermatol.*, vol. 131, pp. 397–405 (1994).
Sampson et al., *J. Allergy Clin. Immunol.*, vol. 81, pp. 635–645 (1988).
H. Tagami, *Jpn. J. Dermatol.*, vol. 106, pp. 955–964 (1996).
Horiuchi et al., *Agic. Biol. Chem.*, vol. 51, pp. 1573–1580 (1987).
Ijzermans et al., *Immunobiology*, vol. 179, pp. 456–473 (1989).
Himmler et al., *J. Interferon Research*, vol. 7, pp. 173–183 (1987).
Devos et al., *J. Interferon Research*, vol. 12, pp. 95–102 (1992).
Hanifin et al., *J. Am. Acad. Dermatol.*, vol. 28, pp. 189–197 (1993).
Reinhold et al., *Lancet*, vol. 335, pp. 1282 (1990).
Reinhold et al., *J. Am. Acad. Dermatol.*, vol. 29, pp. 58–63 (1993).
Zucker, K. et al., *J. Interferon Research*, vol. 13, No. 2, pp. 91–97 (1993).
*Drug Data Report database*, Dialog Accession No. 00168624, accessed Sep. 21, 1998.

* cited by examiner

*Primary Examiner*—Christine Saoud
*Assistant Examiner*—Fozia Hamud
(74) *Attorney, Agent, or Firm*—Birch, Stewart Kolasch & Birch, LLP

(57) ABSTRACT

The present invention relates to a therapeutic agent, composed of canine interferon-γ, for canine intractable dermatitis and a treatment for canine intractable dermatitis using the agent.

21 Claims, No Drawings

THERAPEUTIC AGENT AND TREATMENT FOR CANINE INTRACTABLE DERMATITIS

This application is a continuation-in-part of application Ser. No. 09/001,944 now U.S. Pat. No. 5,955,069 filed on Dec. 31, 1997, the entire contents of which are hereby incorporated by reference.

TECHNICAL FIELD

The present invention relates to a therapeutic agent, composed of canine interferon-γ and a treatment for canine intractable dermatitis using the agent.

BACKGROUND ART

Interferon-γ (hereinafter interferon is referred to as "IFN") is mainly produced by T-cells and is known to have three main functions, i.e., antiviral activity, anti-cell proliferation activity, and immunoregulation (reference 1). With the recent development in gene manipulation techniques, not only human IFN genes but also animal IFN genes, such as bovine, equine, and feline IFN genes have been isolated. Concerning canines, IFN-α, β, and γ have been reported (references 2 and 3). Compared with human or mouse IFN-γ, however, only a little knowledge has been obtained from in vitro and in vivo studies on canine IFN-γ, and there is no report using canine IFN-γ as a therapeutic agent for any particular canine disease.

In humans, IFN-γ has already been put into practical use as a therapeutic agent for malignant tumors. Concerning skin diseases, Hanifin et al. (reference 4) and Rheinhold et al. (references 5 and 6) reported its effectiveness for treating atopic dermatitis and steroid dependent asthma. There is doubt (reference 7), however, regarding the use of human IFN-γ for human atopic dermatitis because of the following reasons: for effectively treating human atopic dermatitis with human IFN-γ, daily administration for 6 consecutive weeks or more is necessary; IFN-γ has adverse effects such as fever and headache and gives the patients a rather large amount of stress while its effects are rather small; and IFN-γ formulations are expensive.

Concerning human dermatitis, diagnosis criteria have been established (reference 8) and a genetic background is regarded as being an important criterion. In addition, human atopic dermatitis is known to be a type I allergic reaction, in which production of an excess amount of IgE in response to foods, animal scales, insect poisons, and the like is an important component (reference 9). However, there have not been any systematic studies done on canine atopic dermatitis. Therefore, the evaluation criteria are unclear and the relationship between the production of excess canine IgE and atopic dermatitis is not clear.

In general, canine skin diseases include eczema, urticaria, allergic dermatitis, traumatic dermatitis, mange, otitis externa, pruritic dermatitis, and the like. The following agents are conventionally used for the above diseases: antihistamines (diphenhydramines), antiphlogistics (dibucaine hydrochloride, etc.), insecticides, and bacteriocides (malathion, benzalkonium chloride, etc.), and steroids (dexamethasone, etc.).

Among therapeutic agents of the prior art used for treating canine skin diseases, however, there are disadvantages in the use of non-steroidal agents as their therapeutic effects are very low. Although steroidal agents have extremely strong pharmacological effects, they occasionally show adverse effects, such as enhancement of infection at disease regions and increases in vascular-wall fragility. Also, long-term administration of steroids may cause obesity or systematic adverse effects as a result of effects on other organs.

In general, canine skin diseases cannot be cured as well as those of humans because of inferior housing conditions. Thus dogs are frequently treated with repeated doses of the above therapeutic agents of the prior art. Treatment periods are thus extended, and occasionally, diseases are not completely cured even if treatment is continued for more than half a year. In some cases, treatment is extended for several years, resulting in great stress for the dog owner. Therefore, there is a demand for a therapeutic agent with a rapid and sustained effect on canine intractable dermatitis that cannot completely be cured by long-term treatment using therapeutic agents of the prior art.

Accordingly, an object of the present invention is to provide an effective therapeutic agent for canine intractable dermatitis.

DISCLOSURE OF THE INVENTION

Inventors of the present invention accomplished the present invention by finding that canine skin diseases, which could hardly be cured by formulations of the prior art, were remarkably improved by administering a canine IFN-γ formulation. In other words, the object of the present invention is to provide a therapeutic agent, containing canine IFN-γ as the active ingredient, for canine intractable dermatitis, and a method for treating canine intractable dermatitis using the therapeutic agent.

BEST MODE FOR CARRYING OUT THE INVENTION

For example, canine IFN-γ of the present invention is a polypeptide having an amino acid sequence shown as SEQ ID NOs:2,4,6,8,10,12,14. However, the present invention includes polypeptides which are within the spirit of the present invention, for example, even if the amino acid sequence has a replacement, insertion, or deletion of one or more amino acid residues, the polypeptide is included in the present invention as long as it shows biological activity of the original IFN-γ as is shown in reference 1. This is because in such a case the polypeptide is regarded as having the effect of the present invention.

Although canine IFN-γ may be produced by an isolation and purification process from natural biomaterials, by chemical synthesis, or by recombinant DNA techniques, the use of canine IFN-γ produced by recombinant DNA techniques is preferable from an economic point of view. The method for producing canine IFN-γ by recombinant DNA techniques is not particularly limited. For example, canine IFN-γ can be produced by using host cells or host animals into which a gene, coding for the whole or part of an amino acid sequence of canine IFN-γ shown in SEQ ID NOs:2,4, 6,8,10,12,14, has been transduced by an already established conventional method. For example, after proliferating *Escherichia coli*, into which cDNA of the whole or part of a base sequence of canine IFN-γ shown in SEQ ID NOs:2, 4,6,8,10,12,14 has been transduced, canine IFN-γ can be obtained from the bacterial cells or supernatants of the bacterial cultures by isolation and purification. Furthermore, after infecting cells of a cultured insect cell line such as *Spondoptera frugiperda* or bombyx mori or silk worms with Baculovirus, into which cDNA of the whole or part of the base sequence of canine IFN-γ shown in SEQ ID NOs:2,4, 6,8,10,12,14 has been transduced, canine IFN-γ can be obtained by purification from the cultured cells, supernatants of cell cultures, or hemolymph of silk worms. In the above cases, the base sequence of canine IFN-γ is not limited to that of SEQ ID NOs:2,4,6,8,10,12,14, as long as it is translated into the amino acid sequence of SEQ ID NOs:2, 4,6,8,10,12,14. In addition, canine IFN-γ having similar effects to the present invention can be produced by using cDNA having a base sequence coding for a poypeptide which is included in the spirit of the present invention, even if the amino acid sequence has a replacement, insertion, or deletion of one or more amino acid residues.

The method for isolating and purifying canine IFN-γ produced by recombinant DNA techniques is not particularly limited, and conventional protein purification methods can be employed. For example, with the antiviral activity of canine IFN-γ as an index, canine IFN-γ can be purified and isolated by combining the following methods for desalting or concentration: chromatography employing silica gel carriers, ion exchange carriers, gel filtration carriers, chelate carriers, pigment ligand carriers, or the like; ultrafiltration; gel filtration; dialysis; salting out; and the like. In the above procedure, the antiviral activity of canine IFN-γ can be measured according to the CPE method of reference 10 using vesicular stomatitis virus (VSV) as the virus and canine MDCK cells (ATCC CCL-34) as the sensitive cells.

In the present invention, canine intractable dermatitis is defined as a group of skin diseases which are not remarkably improved by treatment with therapeutic agents for canine skin diseases of the prior art for at least half a year, or which recur after the symptoms had once been reduced. Examples of the therapeutic agents for treating canine skin disease of the prior art are as follows: exodermatic bacteriocidic disinfectants, antihistamines, steroid hormones, analgesics, antipruritics, astringents, anti-inflammatory agents, and agents for parasitic skin diseases. Frequently, canine intractable dermatitis is not remarkably improved by steroid hormones, or even if the symptoms are reduced, they recur soon after discontinuing the administration. Canine intractable dermatitis includes allergic dermatitis, pemphigus, hypertrophic dermatitis, mycodermatitis, atopic dermatitis, intractable drug eruption, and the like.

In addition to canine IFN-γ, a therapeutic agent for canine intractable dermatitis used in the present invention may optionally contain other components. Components added to the agent are mainly determined by the route of administration. When the agent is used as a solid, for example, fillers such as lactose, binders such as carboxymethyl cellulose and gelatin, coloring agents, and coating agents may be employed; such an agent that is in a solid form may be suitable for oral administration. In addition, the agent can be a formulation which is applied externally to the lesions, such as a cream, a lotion, a latex, and the like, by adding carriers or excipients, such as white petrolatum, cellulose derivatives, surfactants, polyethylene glycol, silicone, or olive oil. When the agent is administered as a liquid, it may contain generally used physiologically acceptable solvents, emulsifiers, and stabilizers. Examples of solvents are water, phosphate buffered saline (PBS), and isotonic physiological saline; examples of emulsifiers are polyoxyethylene surfactants, fatty acid surfactants, and silicone. Examples of stabilizers are proteins, such as canine serum albumin and gelatin, polyols, such as polyethylene glycol and ethylene glycol, and saccharides, such as sorbitol and trehalose. Although the administration route of the therapeutic agent of the present invention is not particularly limited, stronger therapeutic effects can be expected by injection. Any injection method including intravenous administration, intramuscular administration, subcutaneous administration, intraperitoneal administration, and intrapleural administration can be employed, however subcutaneous administration is preferable because it is a simple procedure and causes a lower amount of stress to the patient dogs.

Although the treatment dose is appropriately determined according to the size of the individual, the route of administration, the symptoms, and the like, a dosage sufficient for reducing the symptoms of canine intractable dermatitis is generally administered. For example, administration of 0.002 to 1.0 MU/kg of canine IFN-γ per day provides sufficient effects. Preferably, from an economic and effectiveness point of view, 0.005 to 0.5 MU/kg per day is administered. In the above, kg is the unit of the patient dog weight and U is the unit number determined by the antiviral activity of IFN-γ measured according to the CPE method of reference 10 using vesicular stomatitis virus (VSV) as the virus and canine MDCK cells, (ATCC CCL-34) as the sensitive cells. The amount of IFN-γ that decreases the cytopathic effect of VSV against canine MDCK cells (ATCC CCL-34) by 50% is defined as one unit.

In addition, the frequency of administration is also determined by the individual, the route of administration, the symptoms, and the like. However, it is generally thought that by administration once or twice a week, the symptoms are remarkably reduced at the second week after the beginning of the treatment. Although it is possible to alter the frequency or number of administrations while observing the treatment course, administration twice to ten times every other day or seven days is preferable from the point of view of the amount of stress to the dog owners and the therapeutic effect.

In the method for treatment of the invention, a therapeutic agent of the prior art for treating canine skin diseases can be adjuvantly used in combination. In such a case, the therapeutic agents of the present invention are administered with other agents selected from antihistamines (diphenhydramines), antiphlogistics (dibucaine hydrochloride, etc.), insecticides and bateriocides (malathion, benzalkonium chloride, etc.), steroids (dexamethasone, etc.), and the like.

As is above-mentioned in detail, the present invention provides a therapeutic agent for canine intractable dermatitis having canine IFN-γ as the active ingredient and a treatment method. According to the therapeutic agent and treatment method of the present invention, canine skin diseases which are hardly cured by therapeutic agents for canine dermatitis of the prior art can be treated effectively without adverse effects.

EXAMPLES

The present invention is illustrated in more detail with reference to the following examples, though the present invention is not limited to these examples.

Example 1
Measurement of Antiviral Activity of Canine IFN-γ

Basically, antiviral activity of canine IFN-γ measured according to the method described in reference 10 using canine MDCK (ATCC CCL-34) cells and VSV. Briefly, a diluted solution of a sample containing canine IFN-γ was added to the canine MDCK (ATCC CCL-34) cells, which had been cultured on a 96-well microplate at 37° C. until they reached a confluent state. Then the cells were further incubated at 37° C. for 20 to 24 hours to induce antiviral activity. The cells were mixed with VSV and cultured for 24 hours at 37° C. The living canine MDCK cells that adhered to the microplate were stained with a crystal violet solution containing 20% formalin. The amount of crystal violet on the microplate was determined by measuring the absorbance at 570 nm so as to evaluate the amount of canine IFN-γ at which 50% of the cells were alive. The thus-obtained amount of canine IFN-γ was defined as one unit (1 U) of antiviral activity.

Example 2

Canine IFN-γ Production by *Escherichia coli* Harboring DNA Coding for Canine IFN-γ

In accordance with a conventional method, cDNA of canine IFN-γ having the nucleotide sequence of SEQ. ID. NO. 9 was inserted in pET8c, which is an expression vector for *Escherichia coli*. Then *Escherichia coli* HB101 were transformed by a conventional method. The thus-obtained transformants were inoculated into LB medium containing 100 ug/ml of ampicillin. The transformants were cultured at 37° C. until the $OD_{600}$ reached approximately 0.7. Isopropyl-β-D-thiogalactopyranoside (IPTG) was added to a final concentration of 0.5 mM, and then, the cells were cultured for an additional 1.5 hours. The thus-obtained 11 L of culture medium was centrifuged at 12,000 rpm for 5 min. to separate the supernatant, the residue was suspended in 60 ml of 10 mM tris-Cl (pH 7.5), and the bacterial cells were completely disrupted by sonication on ice. The resultant was centrifuged at 20,000 rpm for 30 min. and the supernatant was recovered to obtain 54 ml of a soluble protein fraction. This fraction had at least $10^6$ U/ml of antiviral activity.

Example 3

Canine IFN-γ Production by *Bombyx mori* Cells or Silk Worms Harboring DNA Coding for Canine IFN-γ

In accordance with a conventional method, cDNA of canine IFN-γ having the nucleotide sequence of SEQ. ID. NO. 1 was transduced into a vector pBM030 (reference 11) to obtain a recombinant plasmid pBMγ. Recombinant Baculoviruses were prepared in accordance with the method of reference 11. Briefly, DNA of both *Bombyx mori* nuclear polyhedrosis virus BmNPV T3 strain (reference 11) and of the recombinant plasmid pBMγ were co-transfected into *Bombyx mori* cells (Bm-N cells) by a calcium phosphate method. Then, recombinant Baculovirus rBNVγ comprising DNA coding for canine IFN-γ was cloned by the limiting dilution method with the following fact as an index: microscopically, when viral infection was observed and when polyhedrin particles were not being formed. Each 0.5 ml of the thus-obtained recombinant virus solution was added to approximately $3 \times 10^6$ Bm-N cells cultured in a TC-100 medium containing 10% FBS in a 25 cm²-tissue culture flask. After 30 min., the medium was replaced with 5 ml of fresh TC-100 medium containing 10% fetal bovine serum (FBS) and cultured at 27° C. for 3 days. The supernatant of the medium was collected by centrifugation and found to have an antiviral activity of $10^4$ U/ml.

Silk worms in the second day of their fifth instar were injected with 50 ul/worm of the liquid of the recombinant Baculovirus rBNVγ comprising DNA coding for canine IFN-γ, fed a commercially available artificial feed (Kanebo Silk Elegance Co.) at 25° C. for 4 days, then the abdomen of ten of these silk worms was cut open to collect their hemolymph into an Eppendorf tube cooled on ice. The resulting hemolymph was centrifuged, and the thus-obtained supernatant was sterilized by filtration using a 0.22 um filter. The resulting supernatant had a measured antiviral activity of $10^7$ U/ml.

Example 4

Preparation of Canine IFN-γ

A 20 mM phosphate buffer (pH 7.0), was used to obtain a two-fold dilution of 50 ml of the soluble protein fraction obtained in EXAMPLE 2. The diluted protein fraction was added to a column packed with 20 ml of silica gel which was equilibrated with the same buffer; the column was washed with a sufficient amount of 20 mM phosphate buffer (pH 7.0). The absorbed components were eluted with 20 mM phosphate buffer (pH 7.0) containing 3 M ammonium chloride and 5% polyethylene glycol to collect a 45 ml eluate. The thus-obtained eluate contained approximately 30 mg of protein and the yield of protein was approximately 30%. After dialyzing 40 ml of the eluate twice with a 10-times volume of 20 mM phosphate buffer (pH 7. 0), the resultant was added to a column packed with 10 ml of SP SEPHAROSE™ FF and the column was washed with 100 ml of 20 mM phosphate buffer (pH 7.0). The absorbed components were eluted by a NaCl concentration gradient to collect eluted fractions containing canine IFN-γ. The thus-obtained eluate fraction contained approximately 15 mg of protein and the purity of the canine IFN-γ was approximately 30%. The eluate was similarly re-chromatographed and the eluate following re-chromatography was desalted by a conventional method using a gel filtration column packed with 80 ml of SEPHADEX™ G-25 to obtain 10 ml of a purified canine IFN-γ fraction. Analysis using SDS-polyacrylamide gel electrophoresis showed that this fraction contained 5 mg of protein and the purity of the canine IFN-γ was at least 80%.

About 2 mg of canine IFN-γ having more than 85% purity was obtained from 100 ml of silkworm hemolymph obtained in Example 3, in which recombinant Baculoviruses were inactivated.

Example 5

Production of a Canine IFN-γ Formulation

A physiological saline for injection, low-molecular gelatin for injection (Nitta Gelatin Inc.), and sorbitol were added to the purified canine IFN-γ solution obtained in EXAMPLE 4 to make a final gelatin concentration of 30%. The resultant was then treated with POSIDYNE (Poll Filtron Co.) to remove pyrogens, and 1 ml per vial of filtrate was added to glass vials sterilized by dry heat at 250° C. for 2 hours. A canine IFN-γ formulation, with each vial containing 0.1 MU to 2.5 MU of canine IFN-γ, was then obtained by lyophilizing aseptically. This canine IFN-γ formulation was stable in the dark at room temperature and highly soluble in water or physiological saline.

Example 6

Treatment of Canine Intractable Dermatitis by Canine IFN-γ

Dogs that had been treated for 0.5 to 7 years with therapeutic agents of the prior art without showing a remarkable reduction in symptoms of skin diseases or exhibiting repeated recurrences were employed for, this study. The subjects of this study included those that had the complication of mycosis supposedly due to adverse effects from steroid hormones. The canine IFN-γ formulation prepared in EXAMPLE 5 was dissolved in 1 ml of physiological saline for injection and administered subcutaneously to the subjects; the therapeutic effects were evaluated by observing the clinical symptoms of skin diseases and adverse effects. Table 1 shows the dose per administration and administration schedule. The severity of canine skin diseases was evaluated as follows: 6 parameters, i.e., erythema, papule, eczema, lichen excoriation, and scale, were scored as 0 (none), 1 (weak), 2 (moderate), and 3 (severe). The total scores of the parameters were defined as the total clinical severity. The therapeutic effects were evaluated from the severity of the clinical symptoms. The therapeutic effects obtained with the canine IFNY-γ formulation prepared from *Escherichia coli* are shown in Table 1. Table 3 shows the therapeutic effect obtained with the formulation of IFN-γ obtained from silk worms.

As is apparent from Tables 1 and 3, in each of the dogs employed for this study the clinical severity of the skin diseases was remarkably reduced, indicating that canine IFNY-γ is extremely effective in the treatment of skin diseases. In addition, the symptoms of the five dogs shown in Table 1 had not been notably reduced by steroid hormone therapy, or had recurred soon after discontinuing the administration of steroid hormones, which is thought to be the most effective among therapeutic agents of the prior art. However, the symptoms were rapidly cured by one or two administrations of canine IFN-γ of the present invention. Furthermore, there were no clinically meaningful adverse effects observed in any of the five dogs.

Example 7
Treatment of Canine Intractable Dermatitis by Canine IFN-γ in Combination with Other Therapeutic Agents Similarly to EXAMPLE 6, dogs that had been treated for at least half a year without showing remarkable reduction in symptoms of skin diseases by therapeutic agents of the prior art or presenting with repeated recurrences were employed for this study. Tests and therapeutic-effect evaluation were carried out according to methods similar to those described in EXAMPLE 6, except that the therapeutic agents shown in Table 2 were used in combination with the canine IFN-γ formulation prepared in EXAMPLE 5. The results in Table 2 show that canine IFN-γ rapidly reduces the clinical symptoms due to canine intractable dermatitis and is effective even when it is used in combination with therapeutic agents of the prior art. In addition, there is a trend that canine IFN-γ exhibits sufficient therapeutic effects at small dose as compared with EXAMPLE 6 when it is used in combination with therapeutic agents of the prior art. Furthermore, adverse effects because of the combined therapy are not particularly observed.

TABLE 1

Therapeutic effects of dog IFN-γ on dog intractable dermatitis (dog IFN-γ alone)

| Test dog No. | Day of administration 1) | Dose of dog IFN-γ (MU/kg) | Severity of clinical symptoms 2) | | | | | | Total clinical severity | Evaluation |
|---|---|---|---|---|---|---|---|---|---|---|
| | | | Erythema | Papule | Eczema | Lichen | Excoriation | Scale | | |
| 1 | 0 | 0.400 | 3 | 3 | 2 | 2 | 1 | 1 | 12 | Very effective |
| | 3 | 0.400 | 3 | 1 | 1 | 0 | 1 | 1 | 7 | |
| | 7 | 0.400 | 1 | 0 | 1 | 0 | 1 | 1 | 4 | |
| | 10 | 0.400 | 0 | 0 | 1 | 0 | 0 | 0 | 1 | |
| | 14 | 0.400 | 0 | 0 | 0 | 0 | 0 | 0 | 0 | |
| | 22 | 0.400 | 0 | 0 | 0 | 0 | 0 | 0 | 0 | |
| 2 | 0 | 0.007 | 3 | 3 | 2 | 1 | 2 | 2 | 13 | Very effective |
| | 7 | 0.007 | 1 | 1 | 1 | 1 | 1 | 1 | 6 | |
| | 16 | 0.007 | 0 | 0 | 0 | 0 | 0 | 0 | 0 | |
| 3 | 0 | 0.003 | 3 | 2 | 2 | 2 | 1 | 1 | 11 | Effective |
| | 4 | 0.003 | 2 | 2 | 1 | 1 | 0 | 0 | 6 | |
| | 8 | 0.003 | 2 | 1 | 1 | 1 | 0 | 0 | 5 | |
| | 11 | 0.003 | 1 | 1 | 1 | 0 | 0 | 0 | 3 | |
| | 17 | 0.003 | 1 | 1 | 0 | 1 | 0 | 0 | 3 | |
| 4 | 0 | 0.008 | 3 | 2 | 3 | 2 | 2 | 1 | 13 | Effective |
| | 7 | 0.030 | 2 | 2 | 1 | 2 | 2 | 1 | 10 | |
| | 19 | 0.016 | 2 | 2 | 1 | 1 | 1 | 1 | 8 | |
| | 27 | 0.008 | 1 | 1 | 0 | 1 | 0 | 1 | 4 | |
| | 34 | 0.004 | 1 | 1 | 0 | 1 | 0 | 1 | 4 | |
| 5 | 0 | 0.007 | 3 | 3 | 2 | 1 | 2 | 1 | 12 | Effective |
| | 8 | 0.004 | 3 | 3 | 1 | 1 | 2 | 1 | 11 | |
| | 15 | 0.004 | 1 | 1 | 1 | 0 | 1 | 0 | 4 | |

1) Day of administration: defined such that the initial day of administration is day 0.
2) Severity of clinical symptoms: 0 (none), 1 (weak), 2 (moderate), and 3 (severe).

TABLE 2

Therapeutic effects of dog IFN-γ on dog intractable dermatitis (combination with conventional therapeutic agent(s))

| Test dog No. | Day of administration 1) | Dose of dog IFN-γ (MU/kg) | Severity of clinical symptoms 2) | | | | | | Total clinical severity | Evaluation | Combined agent(s) |
|---|---|---|---|---|---|---|---|---|---|---|---|
| | | | Erythema | Papule | Eczema | Lichen | Excoriation | Scale | | | |
| 6 | 0 | 0.100 | 3 | 2 | 2 | 1 | 2 | 1 | 11 | Effective | Predonine (4 mg/dog) |
| | 3 | 0.100 | 2 | 1 | 1 | 1 | 1 | 1 | 7 | | None |
| | 7 | 0.100 | 1 | 1 | 1 | 1 | 0 | 0 | 4 | | None |
| | 12 | 0.100 | 1 | 0 | 0 | 1 | 0 | 0 | 2 | | None |
| 7 | 0 | 0.040 | 2 | 3 | 2 | 2 | 1 | 1 | 11 | Very effective | Predonine (4 mg/dog), Lincomycin (50 mg/dog) |
| | 3 | 0.040 | 1 | 2 | 1 | 1 | 1 | 0 | 6 | | None |
| | 5 | 0.040 | 0 | 0 | 0 | 0 | 0 | 0 | 0 | | None |
| 8 | 0 | 0.007 | 3 | 3 | 2 | 1 | 2 | 1 | 12 | Very | Predonine (2.5 mg/dog) |

TABLE 2-continued

Therapeutic effects of dog IFN-γ on dog intractable dermatitis
(combination with conventional therapeutic agent(s))

| Test dog No. | Day of administration 1) | Dose of dog IFN-γ (MU/kg) | Erythema | Papule | Eczema | Lichen | Excoriation | Scale | Total clinical severity | Evaluation | Combined agent(s) |
|---|---|---|---|---|---|---|---|---|---|---|---|
| | 6 | 0.007 | 3 | 2 | 1 | 0 | 1 | 0 | 7 | effective | None |
| | 11 | 0.007 | 0 | 1 | 1 | 0 | 1 | 0 | 3 | | None |
| | 19 | 0.007 | 0 | 0 | 0 | 0 | 1 | 0 | 1 | | Predonine (2.5 mg/dog) |
| | 23 | 0.004 | 0 | 0 | 0 | 0 | 0 | 0 | 0 | | None |
| 9 | 0 | 0.010 | 3 | 2 | 2 | 1 | 2 | 1 | 11 | Effective | Predonine (4 mg/dog), Lincomycin (50 mg/dog) |
| | 3 | 0.010 | 3 | 2 | 1 | 1 | 1 | 0 | 8 | | None |
| | 7 | 0.010 | 2 | 1 | 1 | 0 | 0 | 0 | 4 | | None |
| | 11 | 0.005 | 1 | 1 | 1 | 0 | 1 | 0 | 4 | | None |
| | 19 | 0.002 | 1 | 0 | 1 | 0 | 1 | 0 | 3 | | Predonine (2.5 mg/dog) |
| | 27 | 0.002 | 0 | 1 | 0 | 0 | 1 | 0 | 2 | | Predonine (2.5 mg/dog) |
| 10 | 0 | 0.010 | 3 | 1 | 2 | 2 | 1 | 1 | 10 | Effective | Predonine (10 mg/dog) |
| | 11 | 0.010 | 1 | 1 | 2 | 1 | 1 | 1 | 7 | | Predonine (1 mg/dog) |
| | 18 | 0.010 | 0 | 1 | 1 | 0 | 1 | 0 | 3 | | None |
| 11 | 0 | 0.020 | 3 | 3 | 2 | 3 | 1 | 1 | 13 | Effective | Predonine (1.25 mg/dog) |
| | 6 | 0.020 | 2 | 2 | 1 | 2 | 1 | 0 | 8 | | None |
| | 14 | 0.020 | 2 | 2 | 1 | 1 | 0 | 0 | 6 | | None |
| | 21 | 0.020 | 1 | 1 | 0 | 1 | 0 | 0 | 3 | | None |
| | 28 | 0.020 | 0 | 1 | 0 | 1 | 0 | 0 | 2 | | None |

1) Day of administration: defined such that the initial day of administration is day 0.
2) Severity of clinical symptoms: 0 (none), 1 (weak), 2 (moderate), and 3 (severe).

TABLE 3(1)

Therapeutic effects of dog IFN-γ on dog intractable dermatitis (dog IFN-γ alone)

| Test dog No. | Disease | Day of administration 1) | Dose of dog IFN-γ (MU/kg) | Erythema | Papule | Eczema | Lichen | Excoriation | Scale | Total clinical severity | Evaluation |
|---|---|---|---|---|---|---|---|---|---|---|---|
| 12 | Atopic dermatosis | 0 | 0.030 | 3 | 2 | 3 | 0 | 2 | 0 | 10 | Very effective |
| | | 5 | 0.030 | — | — | — | — | — | — | — | |
| | | 12 | 0.030 | — | — | — | — | — | — | — | |
| | | 16 | 0.030 | — | — | — | — | — | — | — | |
| | | 23 | 0.030 | — | — | — | — | — | — | — | |
| | | 26 | 0.030 | 1 | 1 | 0 | 0 | 0 | 0 | 2 | |
| 13 | Atopic dermatosis | 0 | 0.01 | 2 | 2 | 2 | 0 | 0 | 0 | 6 | Very effective |
| | | 8 | 0.01 | — | — | — | — | — | — | — | |
| | | 14 | 0.01 | — | — | — | — | — | — | — | |
| | | 21 | 0.01 | 0 | 0 | 0 | 0 | 0 | 0 | 0 | |
| 14 | Atopic dermatosis | 0 | 0.002 | 3 | 2 | 2 | 0 | 1 | 0 | 8 | Effective |
| | | 3 | 0.002 | — | — | — | — | — | — | — | |
| | | 6 | 0.002 | — | — | — | — | — | — | — | |
| | | 10 | 0.002 | — | — | — | — | — | — | — | |
| | | 13 | 0.002 | 1 | 0 | 0 | 0 | 0 | 0 | 1 | |
| 15 | Atopic dermatosis | 0 | 0.004 | 3 | 2 | 3 | 0 | 0 | 0 | 8 | Effective |
| | | 3 | 0.004 | — | — | — | — | — | — | — | |
| | | 7 | 0.004 | — | — | — | — | — | — | — | |
| | | 9 | 0.004 | — | — | — | — | — | — | — | |
| | | 19 | 0.004 | 1 | 1 | 0 | 1 | 0 | 0 | 3 | |
| 16 | Pemphigus | 0 | 0.01 | 3 | 3 | 3 | 3 | 3 | 0 | 15 | Effective |
| | | 3 | 0.01 | — | — | — | — | — | — | — | |
| | | 7 | 0.01 | — | — | — | — | — | — | — | |
| | | 10 | 0.01 | — | — | — | — | — | — | — | |
| | | 15 | 0.01 | — | — | — | — | — | — | — | |
| | | 20 | 0.01 | 1 | 1 | 1 | 1 | 1 | 0 | 5 | |

1) Day of administration: defined such that the initial day of administration is day 0.
2) Severity of clinical symptoms: 0 (none), 1 (weak), 2 (moderate), and 3 (severe).

TABLE 3(2)

Therapeutic effects of dog IFN-γ on dog intractable dermatitis (dog IFN-γ alone)

| Test dog No. | Disease | Day of administration 1) | Dose of dog IFN-γ (MU/kg) | Severity of clinical symptoms 2) | | | | | | Total clinical severity | Evaluation |
|---|---|---|---|---|---|---|---|---|---|---|---|
| | | | | Erythema | Papule | Eczema | Lichen | Excoriation | Scale | | |
| 17 | Acanthosis | 0 | 0.010 | 3 | 3 | 3 | 3 | 3 | 3 | 18 | Effective |
| | | 4 | 0.010 | — | — | — | — | — | — | — | |
| | | 7 | 0.010 | — | — | — | — | — | — | — | |
| | | 12 | 0.010 | — | — | — | — | — | — | — | |
| | | 15 | 0.010 | — | — | — | — | — | — | — | |
| | | 19 | 0.010 | 2 | 2 | 2 | 2 | 2 | 2 | 12 | |
| 18 | Chronic dermatosis/ ulcerative dermatosis | 0 | 0.005 | 3 | 3 | 3 | 3 | 3 | 3 | 18 | Very effective |
| | | 3 | 0.005 | — | — | — | — | — | — | — | |
| | | 7 | 0.005 | — | — | — | — | — | — | — | |
| | | 11 | 0.005 | — | — | — | — | — | — | — | |
| | | 15 | 0.005 | — | — | — | — | — | — | — | |
| | | 18 | 0.005 | 0 | 1 | 1 | 0 | 0 | 0 | 2 | |
| 19 | Chronic eczema | 0 | 0.002 | 3 | 2 | 2 | 0 | 1 | 0 | 8 | Effective |
| | | 12 | 0.002 | — | — | — | — | — | — | — | |
| | | 17 | 0.002 | 1 | 1 | 1 | 0 | 0 | 0 | 3 | |
| 20 | Chronic eczema | 0 | 0.002 | 2 | 2 | 2 | 0 | 0 | 2 | 8 | Very effective |
| | | 8 | 0.002 | — | — | — | — | — | — | — | |
| | | 13 | 0.002 | — | — | — | — | — | — | — | |
| | | 9 | 0.002 | — | — | — | — | — | — | — | |
| | | 19 | 0.002 | 1 | 1 | 1 | 0 | 0 | 1 | 4 | |

1) Day of administration: defined such that the initial day of administration is day 0.
2) Severity of clinical symptoms: 0 (none), 1 (weak), 2 (moderate), and 3 (severe).

Example 8
Treatment of Canine Dermatitis by Canine Interferon-γ Mutant

In a conventional way, cDNA for coding canine IFN-γ shown in SEQ ID No. 13 was subcloned into vector pBM030 (reference 11) to obtain recombinant plasmid pBMγS2 (−16). Furthermore, recombinant Baculovirus was prepared according to a method by reference 11. After the DNA of silkworm nuclear polyhedrosis virus BmNPVT3 strain (reference 11) and the DNA of the recombinant plasmid pBMγS2 (−16) were subjected to coinfection in silkworm cells by a calcium phosphate method, recombinant Baculovirus rBNVγS2 (−16) containing DNA for coding the canine IFN-γ was prepared by limiting dilution analysis under indication that virus infection was found by microscopic observation and that no nuclear polyhedron was formed. In the second day of the fifth instar of silkworm larvae, 2 μl/individual of a recombinant Baculovirus rBNVγS2 (−16) solution containing DNA for coding the canine IFN-γ was injected, and the larvae were reared at 25° C. for 5 days while being fed a commercially available artificial feed (made by Kanebo Silk Elegance, Ltd.). Abdominal parts of 50 silkworms were dissected and then immersed in 500 ml of a phosphate buffer solution (pH: 5.0) to extract body fluid. The supernatant obtained by centrifugal separation was sterilized by filtration through a 0.22-μm filter to prepare a body fluid extract of the silkworm. The antiviral activity of the extract was $2.0 \times 10^7$ U/ml.

Through a column packed with 100 ml of SP Sepharose FF (made by Pharmacia) which is equilibrated with a 20-mM phosphate buffer solution (pH: 6.85), 500 ml of silkworm body fluid extract was passed and then washed with 500 ml of a 20-mM phosphate buffer solution (pH: 6.85). The adsorbed component was eluted by NaCl gradient elution to obtain an elution fraction containing the canine IFN-γ. The resulting fraction was passed through a column packed with Blue Sepharose FF (made by Pharmasia) equilibrated with a 20-mM phosphate buffer solution (pH: 6.85), and washed with 50 ml of a 20-mM phosphate buffer solution (pH: 6.85). After it was further washed with 50 ml of a 20-mM phosphate buffer solution (pH: 6.85) containing 100 mM of NaCl, an elution fraction containing the canine IFN-γ was eluted with 50 ml of a 20-mM phosphate buffer solution (pH: 6.85) containing 300 mM of NaCl. The resulting canine IFN-γ had a single band by SDS-PAGE and a purity of 95% or more.

According to amino acid sequence analysis of the canine IFN-γ, it was confirmed to be a canine IFN-γ mutant which lacks 16 amino acid residues from the C-terminus as shown in SEQ ID No. 14.

Using the canine IFN-γ mutant, a lyophilized product was prepared according to the method shown in EXAMPLE 5.

Using the resulting canine IFN-γ mutant preparation, the therapeutic effects were tested with respect to canine dermatitis. After the canine IFN-γ mutant preparation was dissolved into 1 ml of a physiological sodium chloride solution for injection, it was administered by subcutaneous injection. The therapeutic effects were judged by observation of clinical symptoms regarding affected dermal and adverse side effects. As shown in Table 4, therapeutic effects of the canine IFN-γ mutant were also confirmed with respect to canine dermatitis, and no adverse side effects having clinical significance were found in any of the cases.

TABLE 4 therapeutic effects of canine IFN-γ on intractable canine dermatitis (1)

| Tested dog No. | Name of disease | Day of administration | Dose of dog IFN-γ (MU/kg) | Combination | Diagnosis | Evaluation |
|---|---|---|---|---|---|---|
| 1 | Seborrhea | 0 | 0.003 | None | Flare at forelegs and hindlegs, swelling, pruritus, decreased fur, fur humectation | |
| | | 7 | 0.003 | None | Pruritus and flare slightly disappeared | Slightly effective |
| | | 15 | 0.003 | None | Pruritus and flare disappeared. Fur humectation decreased. | Slightly effective |
| | | 28 | 0.003 | None | Pruritus and flare disappeared. Fur humectation decreased. | Effective |
| | | 49 | 0.003 | None | Pruritus and flare disappeared. No fur humectation | Effective |
| | | 66 | 0.003 | None | Pruritus and flare disappeared. No fur humectation | Effective |
| | | 95 | 0.003 | None | Significantly increased fur | Very effective |
| 2 | Pyoderma | 0 | 0.005 | Washing | Erosion from outer ears to parietal region. Significant pruritus and ache | |
| | | 2 | 0.005 | None | Dried erosion and localized flare. Pruritus and ache disappeared. | Very effective |
| | | 6 | 0.005 | None | Almost recovered. | Very effective |
| | | 9 | 0.005 | None | Almost recovered. | Very effective |
| | | 16 | 0.005 | None | Complete recovery. | Very effective |
| 3 | Acanthosis | 0 | 0.004 | None | Black color and pacymenia at venters and inner hindlegs. Strong pruritus | |
| | | 13 | 0.004 | None | Decreased pruritus | Slightly effective |
| | | 26 | 0.004 | None | Decreased pruritus. Increased fur | Effective |
| | | 53 | 0.004 | None | Decreased black pacymenia | Effective |
| 4 | Myco-dermatitis | 0 | 0.002 | Grisovin | Systemic alopesia areata. Pruritus and flare. | — |
| | | 3 | 0.002 | Grisovin | Systemic alopesia areata. Pruritus and flare. | — |
| | | 7 | 0.002 | Grisovin | Flare disappeared. | Slightly effective |
| | | 96 | 0.002 | Grisovin | Flare disappeared. | Slightly effective |
| | | 123 | 0.002 | Grisovin | Increased fur at alopesia areata section | Slightly effective |
| 5 | Atopic dermatitis | 0 | 0.004 | None | Many spiloplaxia and papula at abdominal part and axillary fossa. Significant pruritus and flare. | |
| | | 3 | 0.004 | None | Decreased pruritus and flare. | Effective |
| | | 7 | 0.004 | None | Decreased pruritus and flare. | Effective |
| | | 12 | 0.004 | None | Decreased spiloplaxia and papula. | Effective |
| | | 27 | 0.004 | None | Decreased spiloplaxia and papula. | Effective |
| 6 | Pemphigus | 0 | 0.005 | None | Erosion ulcer at noses and ears. Bleeding. Strong pruritus | |
| | | 4 | 0.005 | None | Decreased pruritus. Decreased erosion. | Slightly effective |
| | | 6 | 0.005 | None | Decreased pruritus. Decreased erosion. | Slightly effective |
| | | 11 | 0.005 | None | Dried erosion. | Effective |
| | | 23 | 0.005 | None | Dried erosion. Increased fur | Effective |

REFERENCES CITED

1. Ijzermans et al.: Immunobiology, 179, 456–473 (1989)
2. Adolf et al.: J. Interferon-Research, 7, 173–183 (1987)
3. Devos et al.: J. Interferon-Research, 12, 95–102 (1992)
4. Hanifin et al.: J. Am. Acad. Dermatol., 28, 189–197 (1993)
5. Rheinhold et al.: Lancet, 335, 1282 (1990)
6. Rheinhold et al.: J. Am. Acad. Dermatol., 29, 58–63 (1993)
7. Nishioka et al.: J. Dermatol., 22, 181–185 (1995)
8. Williams: Br. J. Dermatol., 131, 397–405 (1994)
9. Sampson et al.: J. Allergy Clin. Immunol., 81, 635–645 (1988)
10. Nippon Seikagaku Gakkai (ed): Zoku-Seikagakujikkenkoza, 5, 250–256, Tokyo Kagakudojin (1986)
11. Horiuchi et al.: Agic. Biol. Chem., 51, 1573–1580, (1987)

What is claimed is:

1. A composition for treatment of a canine dermatitis comprising canine interferon-γ lacking 16 amino acids from the C-terminus and a carrier suitable for topical application to the skin.

2. The composition of claim 1, wherein the canine interferon-γ has the amino acid sequence of residues 1 through 127 of SEQ. ID. NO. 14.

3. The composition of claim 1, wherein said canine interferon-γ lacking 16 amino acids from the C-terminus is produced by culturing a cell transformed with a recombinant DNA vector encoding said canine interferon-γ lacking 16 amino acids from the C-terminus, and isolating said canine interferon-γ lacking 16 amino acids from the C-terminus.

4. The composition of claim 1, wherein said canine interferon-γ lacking 16 amino acids from the C-terminus is produced by culturing a cell of *Eschericia coli*, *Bombyx mori* or a cell of a silk worm transformed with a recombinant DNA vector encoding said canine interferon-γ lacking 16 amino acids from the C-terminus, and isolating said canine interferon-γ lacking 16 amino acids from the C-terminus.

5. The composition of claim 1, further comprising an additional protein and/or a saccharide.

6. The composition of claim 4, further comprising an additional protein and/or a saccharide.

7. The composition of claim 1, further comprising a steroid or an anti-allergic agent.

8. A method for treating a canine dermatitis comprising administering a therapeutically effective amount of the composition of claim 1 to a dog suffering from dermatitis.

9. The method of claim 8, wherein said administering is performed by injection.

10. The method of claim 8, wherein said administering is performed at intervals of once per day.

11. The method of claim 8, wherein a steroid or an anti-allergic agent is also administered.

12. The method of claim 8, wherein said canine dermatitis is selected from the group consisting of seborrhea, pyoderma, acanthosis, mycodermatitis, atopic dermatitis and pemphigus.

13. A method for treating a canine dermatitis selected from the group consisting of seborrhea, pyoderma, acanthosis, mycodermatitis, and pemphigus comprising administering to a dog suffering from said dermatitis an amount of a composition comprising canine interferon-γ effective to treat said dermatitis.

14. The method of claim 13, wherein said administering is performed by injection.

15. The method of claim 13, wherein said canine interferon-γ lacks 16 amino acids from the C-terminus and is produced by culturing a cell transformed with a recombinant DNA vector encoding said canine interferon-γ lacking 16 amino acids from the C-terminus, and isolating said canine interferon-γ lacking 16 amino acids from the C-terminus.

16. The method of claim 13, wherein a steroid hormone and/or an anti-allergic agent is also administered.

17. A composition for treatment of a canine dermatitis comprising canine interferon-γ lacking 16 amino acids from the C-terminus and a pharmaceutically acceptable solvent, emulsifier, and/or stabilizer.

18. A method for treating a canine dermatitis comprising administering a therapeutically effective amount of the composition of claim 17 to a dog suffering from dermatitis.

19. The method of claim 18, wherein said administering is performed by injection.

20. The method of claim 18, wherein said administering is performed by subcutaneous injection.

21. The composition of claim 1, wherein said canine interferon-γ lacking 16 amino acids from the C-terminus is produced by culturing a cell transformed with a recombinant DNA vector comprising a polynucleotide having the sequence of SEQ ID NO:13, and isolating the canine interferon-γ lacking 16 amino acids from the C-terminus.

* * * * *

SEQUENCE LISTING

<160> NUMBER OF SEQ ID NOS: 14

<210> SEQ ID NO 1
<211> LENGTH: 498
<212> TYPE: DNA
<213> ORGANISM: Canis sp.
<220> FEATURE:

```
<221> NAME/KEY: CDS
<222> LOCATION: (1)..(498)
<223> OTHER INFORMATION: Canine interferon-gamma
<221> NAME/KEY: sig_peptide
<222> LOCATION: (1)..(69)
<223> OTHER INFORMATION: Method for determining the feature: S
<221> NAME/KEY: mat_peptide
<222> LOCATION: (70)..(498)
<223> OTHER INFORMATION: Method for determining the feature: S

<400> SEQUENCE: 1 atg aat tat aca agc tat atc tta gct ttt cag ctt tgc gtg att ttg      48
Met Asn Tyr Thr Ser Tyr Ile Leu Ala Phe Gln Leu Cys Val Ile Leu
        -20             -15                 -10 tgt tct tct ggc tgt aac tgt cag gcc atg ttt ttt aaa gaa ata gaa      96
Cys Ser Ser Gly Cys Asn Cys Gln Ala Met Phe Phe Lys Glu Ile Glu
     -5              -1   1               5 aac cta aag gaa tat ttt aat gca agt aat cca gat gta tcg gac ggt     144
Asn Leu Lys Glu Tyr Phe Asn Ala Ser Asn Pro Asp Val Ser Asp Gly
 10              15                  20                  25 ggg tct ctt ttc gta gat att ttg aag aaa tgg aga gag agt gac         192
Gly Ser Leu Phe Val Asp Ile Leu Lys Lys Trp Arg Glu Glu Ser Asp
             30                  35                  40 aaa aca atc att cag agc caa att gtc tct ttc tac ttg aaa ctg ttt     240
Lys Thr Ile Ile Gln Ser Gln Ile Val Ser Phe Tyr Leu Lys Leu Phe
 45                  50                  55 gac aac ttt aaa gat aac cag atc att caa agg agc atg gat acc atc     288
Asp Asn Phe Lys Asp Asn Gln Ile Ile Gln Arg Ser Met Asp Thr Ile
         60                  65                  70 aag gaa gac atg ctt ggc aag ttc tta aat agc agc acc agt aag agg     336
Lys Glu Asp Met Leu Gly Lys Phe Leu Asn Ser Ser Thr Ser Lys Arg
 75                  80                  85 gag gac ttc ctt aag ctg att caa att cct gtg aac gat ctg cag gtc     384
Glu Asp Phe Leu Lys Leu Ile Gln Ile Pro Val Asn Asp Leu Gln Val
 90                  95                  100                 105 cag cgc aag gcg ata aat gaa ctc atc aaa gtg atg aat gat ctc tca     432
Gln Arg Lys Ala Ile Asn Glu Leu Ile Lys Val Met Asn Asp Leu Ser
             110                 115                 120 cca aga tcc aac cta agg aag cgg aaa agg agt cag aat ctg ttt cga     480
Pro Arg Ser Asn Leu Arg Lys Arg Lys Arg Ser Gln Asn Leu Phe Arg
 125                 130                 135 ggc cgc aga gca tcg aaa                                             498
Gly Arg Arg Ala Ser Lys
         140

<210> SEQ ID NO 2
<211> LENGTH: 166
<212> TYPE: PRT
<213> ORGANISM: Canis sp.
<223> OTHER INFORMATION: Method for determining the feature: S

<400> SEQUENCE: 2

Met Asn Tyr Thr Ser Tyr Ile Leu Ala Phe Gln Leu Cys Val Ile Leu
        -20             -15                 -10

Cys Ser Ser Gly Cys Asn Cys Gln Ala Met Phe Phe Lys Glu Ile Glu
     -5              -1   1               5

Asn Leu Lys Glu Tyr Phe Asn Ala Ser Asn Pro Asp Val Ser Asp Gly
 10              15                  20                  25

Gly Ser Leu Phe Val Asp Ile Leu Lys Lys Trp Arg Glu Glu Ser Asp
             30                  35                  40

Lys Thr Ile Ile Gln Ser Gln Ile Val Ser Phe Tyr Leu Lys Leu Phe
 45                  50                  55
```

```
Asp Asn Phe Lys Asp Asn Gln Ile Ile Gln Arg Ser Met Asp Thr Ile
         60                  65                  70

Lys Glu Asp Met Leu Gly Lys Phe Leu Asn Ser Ser Thr Ser Lys Arg
     75                  80                  85

Glu Asp Phe Leu Lys Leu Ile Gln Ile Pro Val Asn Asp Leu Gln Val
 90                  95                 100                 105

Gln Arg Lys Ala Ile Asn Glu Leu Ile Lys Val Met Asn Asp Leu Ser
                 110                 115                 120

Pro Arg Ser Asn Leu Arg Lys Arg Lys Arg Ser Gln Asn Leu Phe Arg
             125                 130                 135

Gly Arg Arg Ala Ser Lys
        140

<210> SEQ ID NO 3
<211> LENGTH: 498
<212> TYPE: DNA
<213> ORGANISM: Canis sp.
<220> FEATURE:
<221> NAME/KEY: CDS
<222> LOCATION: (1)..(498)
<223> OTHER INFORMATION: Canine interferon-gamma
<221> NAME/KEY: sig_peptide
<222> LOCATION: (1)..(69)
<223> OTHER INFORMATION: Method for determining the feature: S
<221> NAME/KEY: mat_peptide
<222> LOCATION: (70)..(498)
<223> OTHER INFORMATION: Method for determining feature: S

<400> SEQUENCE: 3 atg aat tat aca agc tat atc tta gct ttt cag ctt tgc gtg att ttg      48
Met Asn Tyr Thr Ser Tyr Ile Leu Ala Phe Gln Leu Cys Val Ile Leu
            -20                 -15                 -10 tgt tct tct ggc tgt aac tgt cag gcc atg ttt ttt aaa gaa ata gaa      96
Cys Ser Ser Gly Cys Asn Cys Gln Ala Met Phe Phe Lys Glu Ile Glu
         -5                  -1   1               5 aac cta aag gaa tat ttt aat gca agt aat cca gat gta tcg gac ggt     144
Asn Leu Lys Glu Tyr Phe Asn Ala Ser Asn Pro Asp Val Ser Asp Gly
 10                  15                  20                  25 ggg tct ctt ttc gta gat att ttg aag aaa tgg aga gag gag agt gac     192
Gly Ser Leu Phe Val Asp Ile Leu Lys Lys Trp Arg Glu Glu Ser Asp
                 30                  35                  40 aaa aca atc att cag agc caa att gtc tct ttc tac ttg aaa ctg ttt     240
Lys Thr Ile Ile Gln Ser Gln Ile Val Ser Phe Tyr Leu Lys Leu Phe
             45                  50                  55 gac aac ttt aaa gat aac cag atc att caa agg agc atg gat acc atc     288
Asp Asn Phe Lys Asp Asn Gln Ile Ile Gln Arg Ser Met Asp Thr Ile
         60                  65                  70 aag gaa gac atg ctt ggc aag ttc tta cag agc agc acc agt aag agg     336
Lys Glu Asp Met Leu Gly Lys Phe Leu Gln Ser Ser Thr Ser Lys Arg
     75                  80                  85 gag gac ttc ctt aag ctg att caa att cct gtg aac gat ctg cag gtc     384
Glu Asp Phe Leu Lys Leu Ile Gln Ile Pro Val Asn Asp Leu Gln Val
 90                  95                 100                 105 cag cgc aag gcg ata aat gaa ctc atc aaa gtg atg aat gat ctc tca     432
Gln Arg Lys Ala Ile Asn Glu Leu Ile Lys Val Met Asn Asp Leu Ser
                 110                 115                 120 cca aga tcc aac cta agg aag cgg aaa agg agt cag aat ctg ttt cga     480
Pro Arg Ser Asn Leu Arg Lys Arg Lys Arg Ser Gln Asn Leu Phe Arg
             125                 130                 135 ggc cgc aga gca tcg aaa                                              498
Gly Arg Arg Ala Ser Lys
```

```
<210> SEQ ID NO 4
<211> LENGTH: 166
<212> TYPE: PRT
<213> ORGANISM: Canis sp.
<223> OTHER INFORMATION: Method for determining feature: S

<400> SEQUENCE: 4

Met Asn Tyr Thr Ser Tyr Ile Leu Ala Phe Gln Leu Cys Val Ile Leu
            -20                 -15                 -10

Cys Ser Ser Gly Cys Asn Cys Gln Ala Met Phe Phe Lys Glu Ile Glu
         -5              -1   1               5

Asn Leu Lys Glu Tyr Phe Asn Ala Ser Asn Pro Asp Val Ser Asp Gly
 10               15              20                  25

Gly Ser Leu Phe Val Asp Ile Leu Lys Lys Trp Arg Glu Glu Ser Asp
             30              35                  40

Lys Thr Ile Ile Gln Ser Gln Ile Val Ser Phe Tyr Leu Lys Leu Phe
                 45              50              55

Asp Asn Phe Lys Asp Asn Gln Ile Ile Gln Arg Ser Met Asp Thr Ile
             60              65              70

Lys Glu Asp Met Leu Gly Lys Phe Leu Gln Ser Ser Thr Ser Lys Arg
     75              80              85

Glu Asp Phe Leu Lys Leu Ile Gln Ile Pro Val Asn Asp Leu Gln Val
 90              95              100                 105

Gln Arg Lys Ala Ile Asn Glu Leu Ile Lys Val Met Asn Asp Leu Ser
                110             115                 120

Pro Arg Ser Asn Leu Arg Lys Arg Lys Arg Ser Gln Asn Leu Phe Arg
            125             130                 135

Gly Arg Arg Ala Ser Lys
        140

<210> SEQ ID NO 5
<211> LENGTH: 498
<212> TYPE: DNA
<213> ORGANISM: Canis sp.
<220> FEATURE:
<221> NAME/KEY: CDS
<222> LOCATION: (1)..(498)
<223> OTHER INFORMATION: Canine interferon-gamma
<221> NAME/KEY: sig_peptide
<222> LOCATION: (1)..(69)
<223> OTHER INFORMATION: Method for determining the feature: S
<221> NAME/KEY: mat_peptide
<222> LOCATION: (70)..(498)
<223> OTHER INFORMATION: Method for determining the feature: S

<400> SEQUENCE: 5 atg aat tat aca agc tat atc tta gct ttt cag ctt tgc gtg att ttg    48
Met Asn Tyr Thr Ser Tyr Ile Leu Ala Phe Gln Leu Cys Val Ile Leu
            -20                 -15                 -10 tgt tct tct ggc tgt aac tgt cag gcc atg ttt ttt aaa gaa ata gaa    96
Cys Ser Ser Gly Cys Asn Cys Gln Ala Met Phe Phe Lys Glu Ile Glu
         -5              -1   1               5 aac cta aag gaa tat ttt cag gca agt aat cca gat gta tcg gac ggt   144
Asn Leu Lys Glu Tyr Phe Gln Ala Ser Asn Pro Asp Val Ser Asp Gly
 10               15              20                  25 ggg tct ctt ttc gta gat att ttg aag aaa tgg aga gag gag agt gac   192
Gly Ser Leu Phe Val Asp Ile Leu Lys Lys Trp Arg Glu Glu Ser Asp
             30              35                  40 aaa aca atc att cag agc caa att gtc tct ttc tac ttg aaa ctg ttt   240
```

```
Lys Thr Ile Ile Gln Ser Gln Ile Val Ser Phe Tyr Leu Lys Leu Phe
            45                  50                  55 gac aac ttt aaa gat aac cag atc att caa agg agc atg gat acc atc      288
Asp Asn Phe Lys Asp Asn Gln Ile Ile Gln Arg Ser Met Asp Thr Ile
            60                  65                  70 aag gaa gac atg ctt ggc aag ttc tta aat agc agc acc agt aag agg      336
Lys Glu Asp Met Leu Gly Lys Phe Leu Asn Ser Ser Thr Ser Lys Arg
 75                  80                  85 gag gac ttc ctt aag ctg att caa att cct gtg aac gat ctg cag gtc      384
Glu Asp Phe Leu Lys Leu Ile Gln Ile Pro Val Asn Asp Leu Gln Val
 90                  95                 100                 105 cag cgc aag gcg ata aat gaa ctc atc aaa gtg atg aat gat ctc tca      432
Gln Arg Lys Ala Ile Asn Glu Leu Ile Lys Val Met Asn Asp Leu Ser
                110                 115                 120 cca aga tcc aac cta agg aag cgg aaa agg agt cag aat ctg ttt cga      480
Pro Arg Ser Asn Leu Arg Lys Arg Lys Arg Ser Gln Asn Leu Phe Arg
            125                 130                 135 ggc cgc aga gca tcg aaa                                              498
Gly Arg Arg Ala Ser Lys
        140
```

<210> SEQ ID NO 6
<211> LENGTH: 166
<212> TYPE: PRT
<213> ORGANISM: Canis sp.
<223> OTHER INFORMATION: Method for determining the feature: S

<400> SEQUENCE: 6

```
Met Asn Tyr Thr Ser Tyr Ile Leu Ala Phe Gln Leu Cys Val Ile Leu
            -20                 -15                 -10

Cys Ser Ser Gly Cys Asn Cys Gln Ala Met Phe Phe Lys Glu Ile Glu
         -5                  -1   1               5

Asn Leu Lys Glu Tyr Phe Gln Ala Ser Asn Pro Asp Val Ser Asp Gly
 10                  15                  20                  25

Gly Ser Leu Phe Val Asp Ile Leu Lys Lys Trp Arg Glu Glu Ser Asp
                 30                  35                  40

Lys Thr Ile Ile Gln Ser Gln Ile Val Ser Phe Tyr Leu Lys Leu Phe
            45                  50                  55

Asp Asn Phe Lys Asp Asn Gln Ile Ile Gln Arg Ser Met Asp Thr Ile
            60                  65                  70

Lys Glu Asp Met Leu Gly Lys Phe Leu Asn Ser Ser Thr Ser Lys Arg
 75                  80                  85

Glu Asp Phe Leu Lys Leu Ile Gln Ile Pro Val Asn Asp Leu Gln Val
 90                  95                 100                 105

Gln Arg Lys Ala Ile Asn Glu Leu Ile Lys Val Met Asn Asp Leu Ser
                110                 115                 120

Pro Arg Ser Asn Leu Arg Lys Arg Lys Arg Ser Gln Asn Leu Phe Arg
            125                 130                 135

Gly Arg Arg Ala Ser Lys
        140
```

<210> SEQ ID NO 7
<211> LENGTH: 498
<212> TYPE: DNA
<213> ORGANISM: Canis sp.
<220> FEATURE:
<221> NAME/KEY: CDS
<222> LOCATION: (1)..(498)
<223> OTHER INFORMATION: Canine interferon-gamma
<221> NAME/KEY: sig_peptide
<222> LOCATION: (1)..(69)
<223> OTHER INFORMATION: Method for determining the feature: S
<221> NAME/KEY: mat_peptide
<222> LOCATION: (70)..(498)
<223> OTHER INFORMATION: Method for determining the feature: S

<400> SEQUENCE: 7

```
atg aat tat aca agc tat atc tta gct ttt cag ctt tgc gtg att ttg      48
Met Asn Tyr Thr Ser Tyr Ile Leu Ala Phe Gln Leu Cys Val Ile Leu
        -20                 -15                 -10 tgt tct tct ggc tgt aac tgt cag gcc atg ttt ttt aaa gaa ata gaa      96
Cys Ser Ser Gly Cys Asn Cys Gln Ala Met Phe Phe Lys Glu Ile Glu
     -5              -1   1                   5 aac cta aag gaa tat ttt cag gca agt aat cca gat gta tcg gac ggt     144
Asn Leu Lys Glu Tyr Phe Gln Ala Ser Asn Pro Asp Val Ser Asp Gly
 10                  15                  20                  25 ggg tct ctt ttc gta gat att ttg aag aaa tgg aga gag gag agt gac     192
Gly Ser Leu Phe Val Asp Ile Leu Lys Lys Trp Arg Glu Glu Ser Asp
                 30                  35                  40 aaa aca atc att cag agc caa att gtc tct ttc tac ttg aaa ctg ttt     240
Lys Thr Ile Ile Gln Ser Gln Ile Val Ser Phe Tyr Leu Lys Leu Phe
             45                  50                  55 gac aac ttt aaa gat aac cag atc att caa agg agc atg gat acc atc     288
Asp Asn Phe Lys Asp Asn Gln Ile Ile Gln Arg Ser Met Asp Thr Ile
         60                  65                  70 aag gaa gac atg ctt ggc aag ttc tta cag agc agc acc agt aag agg     336
Lys Glu Asp Met Leu Gly Lys Phe Leu Gln Ser Ser Thr Ser Lys Arg
     75                  80                  85 gag gac ttc ctt aag ctg att caa att cct gtg aac gat ctg cag gtc     384
Glu Asp Phe Leu Lys Leu Ile Gln Ile Pro Val Asn Asp Leu Gln Val
 90                  95                 100                 105 cag cgc aag gcg ata aat gaa ctc atc aaa gtg atg aat gat ctc tca     432
Gln Arg Lys Ala Ile Asn Glu Leu Ile Lys Val Met Asn Asp Leu Ser
                110                 115                 120 cca aga tcc aac cta agg aag cgg aaa agg agt cag aat ctg ttt cga     480
Pro Arg Ser Asn Leu Arg Lys Arg Lys Arg Ser Gln Asn Leu Phe Arg
            125                 130                 135 ggc cgc aga gca tcg aaa                                             498
Gly Arg Arg Ala Ser Lys
                140
```

<210> SEQ ID NO 8
<211> LENGTH: 166
<212> TYPE: PRT
<213> ORGANISM: Canis sp.
<223> OTHER INFORMATION: Method for determining the feature: S

<400> SEQUENCE: 8

```
Met Asn Tyr Thr Ser Tyr Ile Leu Ala Phe Gln Leu Cys Val Ile Leu
        -20                 -15                 -10

Cys Ser Ser Gly Cys Asn Cys Gln Ala Met Phe Phe Lys Glu Ile Glu
     -5              -1   1                   5

Asn Leu Lys Glu Tyr Phe Gln Ala Ser Asn Pro Asp Val Ser Asp Gly
 10                  15                  20                  25

Gly Ser Leu Phe Val Asp Ile Leu Lys Lys Trp Arg Glu Glu Ser Asp
                 30                  35                  40

Lys Thr Ile Ile Gln Ser Gln Ile Val Ser Phe Tyr Leu Lys Leu Phe
             45                  50                  55

Asp Asn Phe Lys Asp Asn Gln Ile Ile Gln Arg Ser Met Asp Thr Ile
         60                  65                  70
```

```
Lys Glu Asp Met Leu Gly Lys Phe Leu Gln Ser Ser Thr Ser Lys Arg
 75                  80                  85

Glu Asp Phe Leu Lys Leu Ile Gln Ile Pro Val Asn Asp Leu Gln Val
 90                  95                 100                 105

Gln Arg Lys Ala Ile Asn Glu Leu Ile Lys Val Met Asn Asp Leu Ser
                110                 115                 120

Pro Arg Ser Asn Leu Arg Lys Arg Lys Ser Gln Asn Leu Phe Arg
            125                 130                 135

Gly Arg Arg Ala Ser Lys
            140

<210> SEQ ID NO 9
<211> LENGTH: 435
<212> TYPE: DNA
<213> ORGANISM: Canis sp.
<220> FEATURE:
<221> NAME/KEY: CDS
<222> LOCATION: (1)..(435)
<223> OTHER INFORMATION: Canine interferon-gamma
<221> NAME/KEY: mat_peptide
<222> LOCATION: (1)..(435)
<223> OTHER INFORMATION: Method for determining the feature: S

<400> SEQUENCE: 9 atg gct cag gcc atg ttt ttt aaa gaa ata gaa aac cta aag gaa tat      48
Met Ala Gln Ala Met Phe Phe Lys Glu Ile Glu Asn Leu Lys Glu Tyr
 1               5                  10                  15 ttt aat gca agt aat cca gat gta tcg gac ggt ggg tct ctt ttc gta      96
Phe Asn Ala Ser Asn Pro Asp Val Ser Asp Gly Gly Ser Leu Phe Val
                20                  25                  30 gat att ttg aag aaa tgg aga gag gag agt gac aaa aca atc att cag     144
Asp Ile Leu Lys Lys Trp Arg Glu Glu Ser Asp Lys Thr Ile Ile Gln
            35                  40                  45 agc caa att gtc tct ttc tac ttg aaa ctg ttt gac aac ttt aaa gat     192
Ser Gln Ile Val Ser Phe Tyr Leu Lys Leu Phe Asp Asn Phe Lys Asp
        50                  55                  60 aac cag atc att caa agg agc atg gat acc atc aag gaa gac atg ctt     240
Asn Gln Ile Ile Gln Arg Ser Met Asp Thr Ile Lys Glu Asp Met Leu
 65                  70                  75                  80 ggc aag ttc tta aat agc agc acc agt aag agg gag gac ttc ctt aag     288
Gly Lys Phe Leu Asn Ser Ser Thr Ser Lys Arg Glu Asp Phe Leu Lys
                 85                  90                  95 ctg att caa att cct gtc aac gat ctg cag gtc cag cgc aag gcg ata     336
Leu Ile Gln Ile Pro Val Asn Asp Leu Gln Val Gln Arg Lys Ala Ile
                100                 105                 110 aat gaa ctc atc aaa gtg atg aat gat ctc tca cca aga tcc aac cta     384
Asn Glu Leu Ile Lys Val Met Asn Asp Leu Ser Pro Arg Ser Asn Leu
            115                 120                 125 agg aag cgg aaa agg agt cag aat ctg ttt cga ggc cgc aga gca tcg     432
Arg Lys Arg Lys Arg Ser Gln Asn Leu Phe Arg Gly Arg Arg Ala Ser
        130                 135                 140 aaa                                                                  435
Lys
145

<210> SEQ ID NO 10
<211> LENGTH: 145
<212> TYPE: PRT
<213> ORGANISM: Canis sp.
<223> OTHER INFORMATION: Method for determining the feature: S

<400> SEQUENCE: 10
```

```
Met Ala Gln Ala Met Phe Phe Lys Glu Ile Glu Asn Leu Lys Glu Tyr
 1               5                  10                  15

Phe Asn Ala Ser Asn Pro Asp Val Ser Asp Gly Gly Ser Leu Phe Val
                 20                  25                  30

Asp Ile Leu Lys Lys Trp Arg Glu Glu Ser Asp Lys Thr Ile Ile Gln
             35                  40                  45

Ser Gln Ile Val Ser Phe Tyr Leu Lys Leu Phe Asp Asn Phe Lys Asp
         50                  55                  60

Asn Gln Ile Ile Gln Arg Ser Met Asp Thr Ile Lys Glu Asp Met Leu
65                  70                  75                  80

Gly Lys Phe Leu Asn Ser Ser Thr Ser Lys Arg Glu Asp Phe Leu Lys
                 85                  90                  95

Leu Ile Gln Ile Pro Val Asn Asp Leu Gln Val Gln Arg Lys Ala Ile
            100                 105                 110

Asn Glu Leu Ile Lys Val Met Asn Asp Leu Ser Pro Arg Ser Asn Leu
            115                 120                 125

Arg Lys Arg Lys Arg Ser Gln Asn Leu Phe Arg Gly Arg Arg Ala Ser
        130                 135                 140

Lys
145

<210> SEQ ID NO 11
<211> LENGTH: 432
<212> TYPE: DNA
<213> ORGANISM: Canis sp.
<220> FEATURE:
<221> NAME/KEY: CDS
<222> LOCATION: (1)..(432)
<223> OTHER INFORMATION: Canine interferon-gamma
<221> NAME/KEY: mat_peptide
<222> LOCATION: (1)..(432)
<223> OTHER INFORMATION: Method for determining the feature: S

<400> SEQUENCE: 11 atg cag gcc atg ttt ttt aaa gaa ata gaa aac cta aag gaa tat ttt      48
Met Gln Ala Met Phe Phe Lys Glu Ile Glu Asn Leu Lys Glu Tyr Phe
 1               5                  10                  15 aat gca agt aat cca gat gta tcg gac ggt ggg tct ctt ttc gta gat      96
Asn Ala Ser Asn Pro Asp Val Ser Asp Gly Gly Ser Leu Phe Val Asp
                 20                  25                  30 att ttg aag aaa tgg aga gag gag agt gac aaa aca atc att cag agc    144
Ile Leu Lys Lys Trp Arg Glu Glu Ser Asp Lys Thr Ile Ile Gln Ser
             35                  40                  45 caa att gtc tct ttc tac ttg aaa ctg ttt gac aac ttt aaa gat aac    192
Gln Ile Val Ser Phe Tyr Leu Lys Leu Phe Asp Asn Phe Lys Asp Asn
         50                  55                  60 cag atc att caa agg agc atg gat acc atc aag gaa gac atg ctt ggc    240
Gln Ile Ile Gln Arg Ser Met Asp Thr Ile Lys Glu Asp Met Leu Gly
65                  70                  75                  80 aag ttc tta aat agc agc acc agt aag agg gag gac ttc ctt aag ctg    288
Lys Phe Leu Asn Ser Ser Thr Ser Lys Arg Glu Asp Phe Leu Lys Leu
                 85                  90                  95 att caa att cct gtc aac gat ctg cag gtc cag cgc aag gcg ata aat    336
Ile Gln Ile Pro Val Asn Asp Leu Gln Val Gln Arg Lys Ala Ile Asn
            100                 105                 110 gaa ctc atc aaa gtg atg aat gat ctc tca cca aga tcc aac cta agg    384
Glu Leu Ile Lys Val Met Asn Asp Leu Ser Pro Arg Ser Asn Leu Arg
            115                 120                 125 aag cgg aaa agg agt cag aat ctg ttt cga ggc cgc aga gca tcg aaa    432
Lys Arg Lys Arg Ser Gln Asn Leu Phe Arg Gly Arg Arg Ala Ser Lys
        130                 135                 140
```

```
              130                 135                 140

<210> SEQ ID NO 12
<211> LENGTH: 144
<212> TYPE: PRT
<213> ORGANISM: Canis sp.
<223> OTHER INFORMATION: Method for determining the feature: S

<400> SEQUENCE: 12

Met Gln Ala Met Phe Phe Lys Glu Ile Glu Asn Leu Lys Glu Tyr Phe
 1               5                  10                  15

Asn Ala Ser Asn Pro Asp Val Ser Asp Gly Gly Ser Leu Phe Val Asp
             20                  25                  30

Ile Leu Lys Lys Trp Arg Glu Glu Ser Asp Lys Thr Ile Ile Gln Ser
         35                  40                  45

Gln Ile Val Ser Phe Tyr Leu Lys Leu Phe Asp Asn Phe Lys Asp Asn
     50                  55                  60

Gln Ile Ile Gln Arg Ser Met Asp Thr Ile Lys Glu Asp Met Leu Gly
 65                  70                  75                  80

Lys Phe Leu Asn Ser Ser Thr Ser Lys Arg Glu Asp Phe Leu Lys Leu
                 85                  90                  95

Ile Gln Ile Pro Val Asn Asp Leu Gln Val Gln Arg Lys Ala Ile Asn
            100                 105                 110

Glu Leu Ile Lys Val Met Asn Asp Leu Ser Pro Arg Ser Asn Leu Arg
        115                 120                 125

Lys Arg Lys Arg Ser Gln Asn Leu Phe Arg Gly Arg Arg Ala Ser Lys
    130                 135                 140

<210> SEQ ID NO 13
<211> LENGTH: 450
<212> TYPE: DNA
<213> ORGANISM: Canis sp.
<220> FEATURE:
<221> NAME/KEY: CDS
<222> LOCATION: (1)..(450)
<223> OTHER INFORMATION: Canine interferon-gamma
<221> NAME/KEY: sig_peptide
<222> LOCATION: (1)..(69)
<223> OTHER INFORMATION: Method for determining the feature: S
<221> NAME/KEY: mat_peptide
<222> LOCATION: (70)..(450)
<223> OTHER INFORMATION: Method for determining the feature: S

<400> SEQUENCE: 13 atg aat tat aca agc tat atc tta gct ttt cag ctt tgc gtg att ttg      48
Met Asn Tyr Thr Ser Tyr Ile Leu Ala Phe Gln Leu Cys Val Ile Leu
            -20                 -15                 -10 tgt tct tct ggc tgt aac tgt cag gcc atg ttt ttt aaa gaa ata gaa      96
Cys Ser Ser Gly Cys Asn Cys Gln Ala Met Phe Phe Lys Glu Ile Glu
        -5                  -1  1                   5 aac cta aag gaa tat ttt cag gca agt aat cca gat gta tcg gac ggt     144
Asn Leu Lys Glu Tyr Phe Gln Ala Ser Asn Pro Asp Val Ser Asp Gly
 10                  15                  20                  25 ggg tct ctt ttc gta gat att ttg aag aaa tgg aga gag gag agt gac     192
Gly Ser Leu Phe Val Asp Ile Leu Lys Lys Trp Arg Glu Glu Ser Asp
                 30                  35                  40 aaa aca atc att cag agc caa att gtc tct ttc tac ttg aaa ctg ttt     240
Lys Thr Ile Ile Gln Ser Gln Ile Val Ser Phe Tyr Leu Lys Leu Phe
             45                  50                  55 gac aac ttt aaa gat aac cag atc att caa agg agc atg gat acc atc     288
Asp Asn Phe Lys Asp Asn Gln Ile Ile Gln Arg Ser Met Asp Thr Ile
         60                  65                  70
```

```
aag gaa gac atg ctt ggc aag ttc tta cag agc agc acc agt aag agg      336
Lys Glu Asp Met Leu Gly Lys Phe Leu Gln Ser Ser Thr Ser Lys Arg
    75                  80                  85 gag gac ttc ctt aag ctg att caa att cct gtg aac gat ctg cag gtc      384
Glu Asp Phe Leu Lys Leu Ile Gln Ile Pro Val Asn Asp Leu Gln Val
 90                  95                 100                 105 cag cgc aag gcg ata aat gaa ctc atc aaa gtg atg aat gat ctc tca      432
Gln Arg Lys Ala Ile Asn Glu Leu Ile Lys Val Met Asn Asp Leu Ser
                110                 115                 120 cca aga tcc aac cta agg                                              450
Pro Arg Ser Asn Leu Arg
            125

<210> SEQ ID NO 14
<211> LENGTH: 150
<212> TYPE: PRT
<213> ORGANISM: Canis sp.
<223> OTHER INFORMATION: Method for determining the feature: S

<400> SEQUENCE: 14

Met Asn Tyr Thr Ser Tyr Ile Leu Ala Phe Gln Leu Cys Val Ile Leu
            -20                 -15                 -10

Cys Ser Ser Gly Cys Asn Cys Gln Ala Met Phe Phe Lys Glu Ile Glu
         -5                  -1   1               5

Asn Leu Lys Glu Tyr Phe Gln Ala Ser Asn Pro Asp Val Ser Asp Gly
 10                  15                  20                  25

Gly Ser Leu Phe Val Asp Ile Leu Lys Lys Trp Arg Glu Glu Ser Asp
                 30                  35                  40

Lys Thr Ile Ile Gln Ser Gln Ile Val Ser Phe Tyr Leu Lys Leu Phe
             45                  50                  55

Asp Asn Phe Lys Asp Asn Gln Ile Ile Gln Arg Ser Met Asp Thr Ile
             60                  65                  70

Lys Glu Asp Met Leu Gly Lys Phe Leu Gln Ser Ser Thr Ser Lys Arg
    75                  80                  85

Glu Asp Phe Leu Lys Leu Ile Gln Ile Pro Val Asn Asp Leu Gln Val
 90                  95                 100                 105

Gln Arg Lys Ala Ile Asn Glu Leu Ile Lys Val Met Asn Asp Leu Ser
                110                 115                 120

Pro Arg Ser Asn Leu Arg
            125
```